United States Patent
Letort (10) Patent No.: US 6,918,926 B2
(45) Date of Patent: Jul. 19, 2005

(54) SYSTEM FOR TRANSRENAL/INTRAOSTIAL FIXATION OF ENDOVASCULAR PROSTHESIS

(75) Inventor: Michel Letort, Larkspur, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/133,190

(22) Filed: Apr. 25, 2002

(65) Prior Publication Data

US 2003/0204240 A1 Oct. 30, 2003

(51) Int. Cl.[7] .................................................. A61F 2/06
(52) U.S. Cl. .................... 623/1.13; 623/1.15; 623/1.16; 623/1.36
(58) Field of Search ............................. 623/1.11, 1.12, 623/1.13, 1.15, 1.36, 1.16

(56) References Cited

U.S. PATENT DOCUMENTS

| | | | | |
|---|---|---|---|---|
| 5,527,355 A | * | 6/1996 | Ahn | 623/1.36 |
| 5,713,917 A | | 2/1998 | Leonhardt et al. | 606/194 |
| 5,720,776 A | * | 2/1998 | Chuter et al. | 623/1.36 |
| 5,824,041 A | | 10/1998 | Lenker et al. | 623/1 |
| 5,868,777 A | * | 2/1999 | Lam | 606/194 |
| 5,984,955 A | * | 11/1999 | Wisselink | 623/1.35 |
| 5,993,481 A | * | 11/1999 | Marcade et al. | 623/1.35 |
| 6,165,212 A | * | 12/2000 | Dereume et al. | 623/1.13 |
| 6,283,991 B1 | * | 9/2001 | Cox et al. | 623/1.13 |
| 6,428,565 B1 | * | 8/2002 | Wisselink | 623/1.11 |
| 6,451,048 B1 | * | 9/2002 | Berg et al. | 623/1.13 |
| 6,475,232 B1 | * | 11/2002 | Babbs et al. | 623/1.13 |
| 6,524,335 B1 | * | 2/2003 | Hartley et al. | 623/1.13 |

* cited by examiner

Primary Examiner—Corrine McDermott
Assistant Examiner—Kamrin Landrem (57) ABSTRACT

An endoluminal prosthesis is provided with an improved fixation system for coupling the endoluminal prosthesis to an inner wall of a lumen and to reduce distal migration. According to an embodiment of the present invention, a laterally protruding member atraumatically engages the ostium of a side or branch vessel. The protruding member may be fixed to a portion of a prosthesis. In one embodiment the protruding member is provided on a modular fixation device for initial fixation within the body lumen with the finger member within the side or branch vessel. A primary endoluminal prosthesis is then fixed to the modular fixation device to bypass a diseased portion of the anatomy.

26 Claims, 8 Drawing Sheets

SYSTEM FOR TRANSRENAL/INTRAOSTIAL FIXATION OF ENDOVASCULAR PROSTHESIS

FIELD OF THE INVENTION

The present invention relates to tubular prostheses such as grafts and endoluminal prostheses including, for example, stent-grafts and aneurysm exclusion devices, and methods for placement of such grafts and endoluminal structures. In particular, the present invention relates to a system for intraostial endoluminal prosthesis fixation.

BACKGROUND OF THE INVENTION

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

A number of vascular devices have been developed for replacing, supplementing or excluding portions of blood vessels. These vascular grafts may include but are not limited to endoluminal vascular prostheses and stent grafts, for example, aneurysm exclusion devices such as abdominal aortic aneurysm ("AAA") devices that are used to exclude aneurysms and provide a prosthetic lumen for the flow of blood. Typically these endoluminal prostheses or stent grafts are constructed of graft materials such as woven polymer materials (e.g., Dacron,) or polytetrafluoroethylene ("PTFE") and a support structure. The stent-grafts typically have graft material such as a woven polymer, secured onto the inner diameter or outer diameter of a support structure that supports the graft material and/or holds it in place against a luminal wall.

One very significant use for endoluminal or vascular prostheses is in treating aneurysms. Vascular aneurysms are the result of abnormal dilation of a blood vessel, usually resulting from disease or a genetic predisposition, which can weaken the arterial wall and allow it to expand. While aneurysms can occur in any blood vessel, most occur in the aorta and peripheral arteries, with the majority of aneurysms occurring in the abdominal aorta. Typically an abdominal aneurysm will begin below the renal arteries and may extend into one or both of the iliac arteries.

Aneurysms, especially abdominal aortic aneurysms, have been treated in open surgery procedures where the diseased vessel segment is bypassed and repaired with an artificial vascular graft. While considered to be an effective surgical technique in view of the alternative of a fatal ruptured abdominal aortic aneurysm, the open surgical technique suffers from a number of disadvantages. The surgical procedure is complex and requires long hospital stays due to serious complications and long recovery times and has high mortality rates. In order to reduce the mortality rates, complications and duration of hospital stays, less invasive devices and techniques have been developed. The improved devices include tubular prostheses that provide a lumen or lumens for blood flow while excluding blood flow to the aneurysm site. They are introduced into the blood vessel using a catheter in a less or minimally invasive technique. Although frequently referred to as stent-grafts, these devices differ from covered stents in that they are not used to mechanically prop open natural blood vessels. Rather, they are used to secure an artificial lumen in a sealing engagement with the vessel wall without further opening the natural blood vessel that is already abnormally dilated.

Most currently used AAA devices comprise a main body portion fixed at the infrarenal aorta junction. The prostheses are typically secured to a vessel wall above and below the aneurysm site with at least one attached expandable annular spring member that provides sufficient radial force so that the prosthesis engages the inner lumen wall of the body lumen to seal the prosthetic lumen from the aneurysm. The devices are typically delivered by initially placing a main body endoluminally and engaging the device to the aorta wall by a series of self-expanding annular spring members. The main body is frequently a bifurcated device with a long and short iliac leg for directing blood flow through the iliac arteries. A contralateral leg is delivered and coupled to the short leg of the bifurcated main body graft. Iliac and/or aortic cuffs then may be delivered if desired to improve or extend deployment or fixation through desired regions.

In general, in many diseased vessels, the area for prosthesis fixation above an aneurysm or other diseased portion may be limited, making secure fixation of the prosthesis more difficult. In addition, over time there is a possibility that the prosthesis may migrate. A number of devices or solutions have been proposed to improve fixation. Super renal fixation has been provided to improve fixation. However, particularly in a diseased patient, there may be suprarenal cholesterol or atheroma plagues that may dislodge, fragment or release from the supra renal area. In other devices, other mechanisms have also been used to engage the vessel walls such as, for example, hook like members that puncture the vessel wall. The hooks traumatize the tissue and therefore may be undesirable. Increased radial force has been proposed to improve fixation as well. However, in some patients, migration may occur when the neck or region in which the graft is deployed expands or otherwise changes over time and thus increased radial force may not prevent migration in such a situation.

It would accordingly be desirable to provide a stent graft fixation system that provides improved fixation with a confined or limited area upstream of an aneurysm site. It would also be desirable to provide a device that reduces migration of the stent graft. It would also be desirable to provide an improved fixation system for an endoluminal prosthesis that reduces trauma to tissue.

SUMMARY OF THE INVENTION

An embodiment according to the present invention provides an endoluminal prosthesis with an improved fixation system for deploying the endoluminal prosthesis within a body lumen and reducing distal migration of the prosthesis. The fixation system comprises at least one laterally extending member or finger member extending from a portion of a prosthesis, where the finger member is to be deployed within a proximal branch lumen. The finger member may be incorporated into the main prosthesis or may be included with a modular portion of the prosthesis such as a short cuff that is initially deployed within the body lumen, with the longer main prosthesis subsequently fixed to the cuff. The finger member is configured to be non-piercing or relatively atraumatic to tissue. The finger member may be a self-expanding so that it tends to open or extend laterally when not constrained. In one embodiment, the finger member extends laterally at about 90 degrees from the prosthesis.

In one embodiment a modular fixation device or cuff is provided with at least one intraostial finger member. The cuff is configured for initial fixation to a lumen wall. A longer endoluminal prosthesis is provided and is coupled to the cuff to bypass a diseased portion of the anatomy. The cuff may provide a more reliable landing zone for the prosthesis and a more predictable, consistent engagement area, while the finger further prevents distal migration of the cuff. In one embodiment, the cuff comprises one or more support structures and a graft material surrounding at least a portion of a support structure. The cuff is arranged to engage the inner lumen wall at a fixation site and form a leak resistant seal with the inner wall of the body lumen. The finger member when deployed extends laterally from the sidewall of the tubular member and into the branch vessel.

The cuff and finger member initially secure the proximal fixation area. Then, when an adequate seal and fixation is made available through the cuff and finger member, the main body of the prosthesis is delivered inside the cuff and deployed in a manner that provides fixation and seal between the prosthesis and the cuff. An example of such cuff and prosthesis is described in U.S. application entitled "ENDOVASCULAR STENT GRAFT AND FIXATION CUFF" filed on Apr. 25, 2002 and incorporated herein by reference.

In one embodiment, the prosthesis is constructed of a tubular graft material (such as a woven polymer for conducting fluid) supported by annular spring members. According to one variation, the finger member is coupled to the cuff and is constructed of a loop of a spring like material such as a Nickel Titanium alloy having superelastic properties. The finger member may also be coated by a material such as a polymer film to protect adjacent tissue. The finger member has one portion coupled to the prosthesis (for example, by welding onto the annular spring member) and a free end that is free from the prosthesis. The spring finger member tends towards a lateral position with respect to the sidewall of the prosthesis. Prior to deployment, the finger member is confined or restrained into a position substantially parallel to the prosthesis sidewall. When initially, partially deployed, the finger member is released and positioned above or at an ostium of a branch vessel. The prosthesis, partially deployed and partially retained by a deliver catheter, is drawn distally with the catheter and the free end of the finger member is positioned over the ostium, it springs towards an open position and catches the, ostium. The prosthesis is drawn distally until the finger member is located within the branch vessel and then is fully released from the catheter.

When deployed, the annular members of the prosthesis expand to maintain the prosthesis in a conformed, sealing arrangement with the inner wall of the body lumen. The finger member is positioned so that the free end is within the ostium of a side branch vessel as described above. If the prosthesis is a fixation cuff, an endoluminal prosthesis is then deployed within the cuff. The annular members of the prosthesis support the tubular graft and maintain the lumen provided by the prosthesis, open and in a conformed, sealing arrangement with the inner wall of the cuff, providing a lumen through which body fluids may flow.

The annular support members each comprise an annular expandable member formed by a series of connected compressible diamond structures. The finger member is preferably coupled to the proximal most annular support member and may be integrally formed therewith so that it extends about 1 or 2 millimeters above the renal ostium, which is not to be blocked by the prosthesis. Alternatively, for example, the expandable member may be formed of an undulating or sinusoidal-like patterned wire ring or other compressible spring member. Preferably the annular support members are radially compressible springs biased in a radially outward direction, which when released, bias the prosthesis into conforming fixed engagement with an interior surface of the vessel. Annular support members are used to create a seal between the prosthesis and the inner wall of a body lumen, as well as to support the tubular graft structures. The annular springs are preferably constructed of Nitinol. Examples of such annular support structures are described, for example, in U.S. Pat. Nos. 5,713,917 and 5,824,041 incorporated herein by reference. When used in an aneurysm exclusion device, the springs have sufficient radial spring force and flexibility to conformingly engage the body lumen inner wall to avoid excessive leakage, and prevent pressurization of the aneurysm, i.e., to provide a leak resistant seal. Although some leakage of blood or other body fluid may occur into the aneurysm isolated by the prosthesis, an optimal seal will reduce the chances of aneurysm pressurization and the possible resulting rupture. The annular support members are attached or mechanically coupled to the graft material along the tubular graft by various means, such as, for example, by stitching onto either the inside or outside of the tubular graft.

An aneurysm exclusion device according to the invention may be used in other regions such as the thoracic region.

The endoluminal prosthesis may be in the form of either a straight single-limb tubular member or a generally Y-shaped bifurcated tubular member having a trunk joining at a graft junction with a pair of lateral limbs, namely an ipsilateral limb and a contralateral limb. In an abdominal aneurysm, a bifurcated device is frequently preferred. In such a bifurcated prosthesis, the proximal portion of the prosthesis comprises a trunk with a proximal opening, and a distal portion branched into at least two branches with distal openings. Thus, body fluids may flow from the proximal opening through the distal openings of the branches. Preferably the ipsilateral limb is longer so that when deployed, it extends into the common iliac. A single limb extension member is provided having a mating portion for coupling with a lateral limb of a bifurcated member and an adjustable length portion extending coaxially from a distal end of the mating portion.

The compressed profile of the prosthesis with the finger member is sufficiently low to allow the prosthesis to be placed into the vasculature using a low profile delivery catheter. The prosthesis can be placed within a diseased vessel via deployment means at the location of an aneurysm. Various means for delivery of a prosthesis through the vasculature to the site for deployment, are well known in the art and may be found for example is U.S. Pat. Nos. 5,713, 917 and 5,824,041. In general, the prosthesis is radially compressed and loaded in or on the distal end of the catheter for delivery to the deployment site. The aneurysm site is located using an imaging technique such as fluoroscopy, and the catheter is guided through a femoral iliac artery with the use of a guide wire to the aneurysm site.

A guide wire may be initially inserted through the femoral artery to the aorta and into the renal artery where the finger of the prosthesis is to be deployed. This may assist in locating the distal end of the sheath at the ostium of the renal artery where the finger member of the prosthesis is to be deployed Once appropriately located, a sheath on the catheter covering or restraining the prosthesis is retracted to release the finger member. Once the finger member is appropriately located in the ostium, the sheath may be further retracted releasing the prosthesis, allowing the annular springs to expand and attach or engage the prosthesis to the inner wall of the body lumen. Alternatively, the prosthesis may be positioned and released with the finger member slightly above the ostium. The finger member expands when released and may be constrained to some extent by the inner wall of the lumen. The free end of the finger member is located at the ostium of a branch vessel by drawing the prosthesis distally until the finger member is located in the ostium. Once the finger member is in position, the prosthesis may be fully deployed and released from the catheter. A marker may be placed on the prosthesis so that the circumferential orientation of the finger member may be determined for positioning it at the ostium of the side or branch vessel.

These and further aspects of the invention are exemplified and in the detailed description of embodiments according to the invention described below.

DETAILED DESCRIPTION

FIGS. 1A–8 illustrate various embodiments of a cuff with a finger member or extension, and endoluminal prosthesis, a delivery system and a method according to the present invention. Although a fixation cuff, endoluminal prosthesis, delivery system and method according to the invention may be used in any body lumen that conducts body fluid and may be used as a single lumen prosthesis or a multibranch prosthesis, they are described herein with reference to treatment of an aortic aneurysm, in particular in the abdomen of a patient using a bifurcated prosthesis.

FIGS. 1A–3 and 7 illustrate an embodiment of a fixation cuff according to the present invention. The cuff 110 comprises a tubular graft layer 115, a series of radially compressible annular support members 112 attached to the tubular graft layer 115, and a finger member 116 extending laterally of the proximal most support member 112a. The finger member 116 is welded to the proximal most support member 112a and is configured to extend 1 or 2 millimeters above the cuff 110 when in its deployed position. The annular support members 112 are attached to the tubular graft member 115 using sutures or other coupling means. The cuff 110 is generally between about 5 and 20 mm in length so that when the finger is located in a renal artery, it may be placed from the aorta renal junction and extend towards the aortic aneurysm 18. The cuff 110 provides an inner circumferential area to which the prosthesis 210 may be secured.

The finger member 116 is preferably a spring loop made of a Nitinol wire and having a thin layer or film about the wire loop to provide a relatively atraumatic member and to protect adjacent tissue. The finger member 116 has a first portion comprised of members 117a, 117b attached to the distal portion of the support member 112a, and coupled by spring loops 118a, 118b to a free end 119, free from the cuff 110. The finger member 116 is shape set to a position extending laterally from the centerline of the cuff 110. The spring loops 118a, 118b provide flexibility to the finger member 116 and also permit variations in length of the finger member 116. The finger member 116, when loaded in a catheter or otherwise restrained, is compressed into a position that is substantially parallel to the sidewall 115a of the tubular graft 115. In this position, the free end 119 extends towards the distal portion 110d of the cuff 110. When released, the free end 119 tends to spring towards a position extending laterally of the sidewall 115a of the tubular graft 115.

The annular support members 112 are preferably spring members having predetermined radii and are preferably constructed of a material such as Nitinol in a superelastic, straight annealed condition. The support members 112 comprise a series of connected diamond structures. 111 around the circumference of the annular member 112 that form peaks 113 and valleys 114. Other annular support structures may be used as well, such as a sinusoidal or undulating wire spring member. In FIGS. 1A–3, the annular support members 112 are in an expanded position. Prior to deployment the annular members 112 are compressed. The annular members 112 are configured to support the cuff 110 and/or bias the cuff 110 into conforming fixed engagement with the inner wall of the aorta 10.

The tubular graft 115 is preferably formed of a biocompatible material with a textured inner surface such as velour so that it better engages the outer circumference of a prosthesis fixed to the cuff 110 and provides a better seal. Alternatively or in addition, an outer tubular graft may also be provided and may be formed of a textured surface such as velour to better engage the inner wall of the aorta 10 and provide a better seal. The velour also is a low porosity woven fabric to provide a leak resistant seal. The graft material is relatively thin-walled so that it may be compressed into a small diameter, yet capable of acting as a strong, leak-resistant, fluid conduit when in tubular form.

Referring to FIGS. 1A–3, the cuff 110 is illustrated located in an aorta 10 after being deployed by a catheter. The aorta 10 is joined by renal arteries 12 and 14 at the aorto-renal junction 16. In the ostia 22, 24 (the portion of the renal arteries 12, 14 respectively where the aorta 10 joins the arteries 12, 14) the arteries 12, 14 are slightly enlarged. Just below the aorta-renal junction 16 is an aneurysm 18, a diseased region where the vessel wall is weakened and expanded. Below the aneurysm 18, the aorta 10 bifurcates into right and left iliac vessels 11, 13, respectively. The finger member 116 is to be located, for example, within one of the renal arteries 12, 14. The renal arteries 12, 14 typically are not directly across from each other, one being located distal of the other. The finger member 116 is preferably to be placed in the distal-most renal artery 14 so that the cuff 110 does not block either of the renal arteries 12, 14. The selection of the renal artery into which the finger 116 is deployed may occur prior to surgery using imaging to determine which renal artery would be appropriate for this purpose.

Figure 1A:
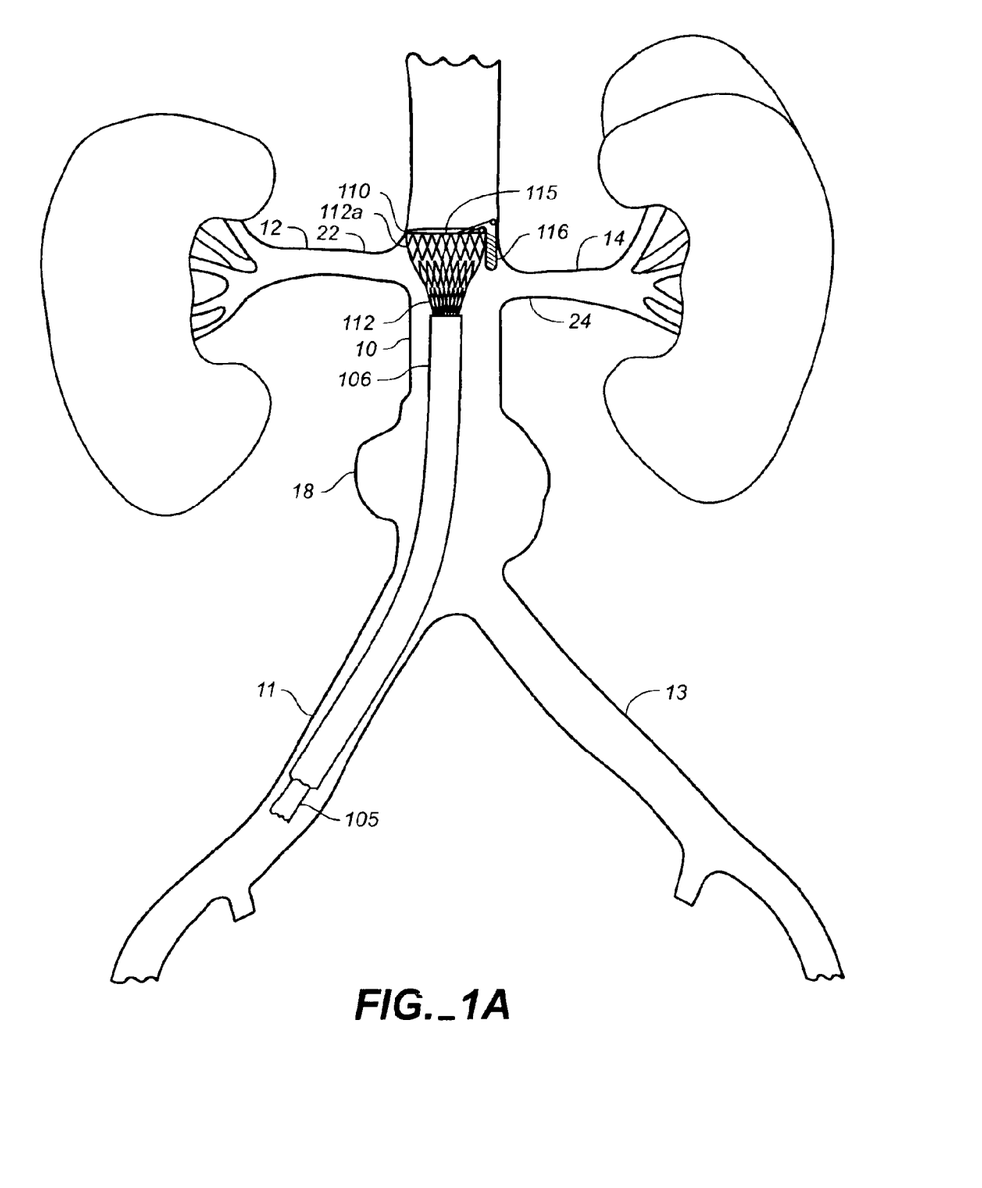
FIG. 1A is a side view of a cuff according to an embodiment according to the invention initially deployed in an aorta, proximal of its intended final deployment position.
Figure 1B:
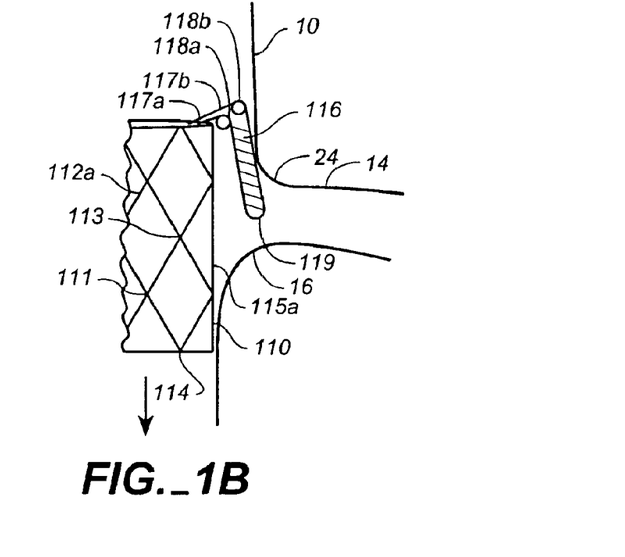
FIG. 1B is an enlarged perspective view of a portion of the cuff and anatomy of FIG. 1A.

Referring to FIG. 1A, the prosthesis, in the embodiment a cuff 110, is delivered into the abdominal aorta 10 using a catheter 105 including a sheath 106 used to retrain the cuff 110 until deployed. In FIG. 1A, the cuff 110 is partially deployed within an aorta 10 above the aneurysm 18 by partially retracting the sheath 106. The proximal most portion 110a of the cuff 110 is located above the renal artery 14, which in this instance is the distal most of the renal arteries 12, 14. The finger 116 is located above the renal artery 14, which defines an ostium 24 at its junction with the aorta 10. The free end 119 of the finger member 116 is just proximal of the ostium 24.

Figure 2:
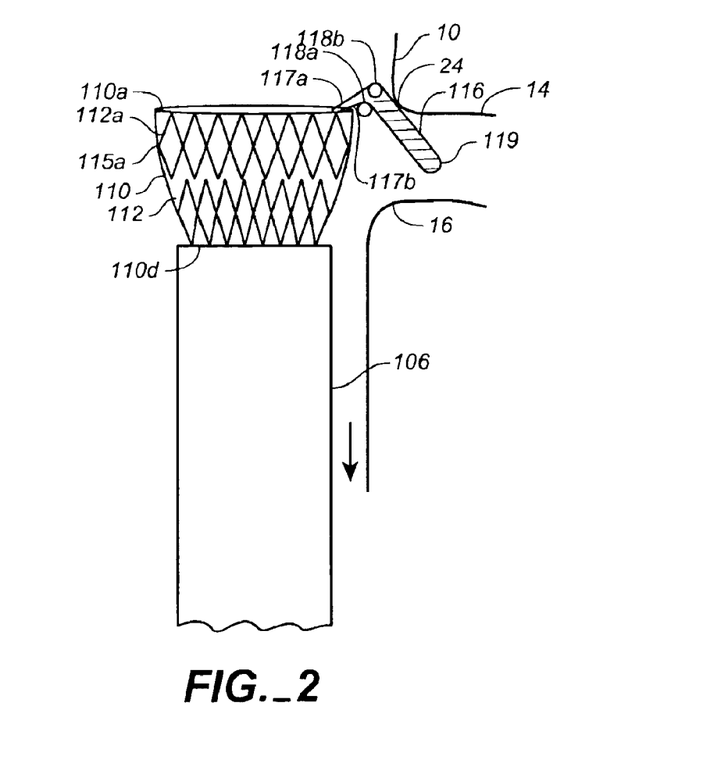
FIG. 2 is a perspective view of a portion of the cuff of FIG. 1A with the free end of the finger located at the ostium of a renal artery.

Referring to FIG. 2, the cuff 110 is drawn in a proximal direction until the free end 119 is at the opening into the ostium 24 where it catches the ostium 24

Figure 3:
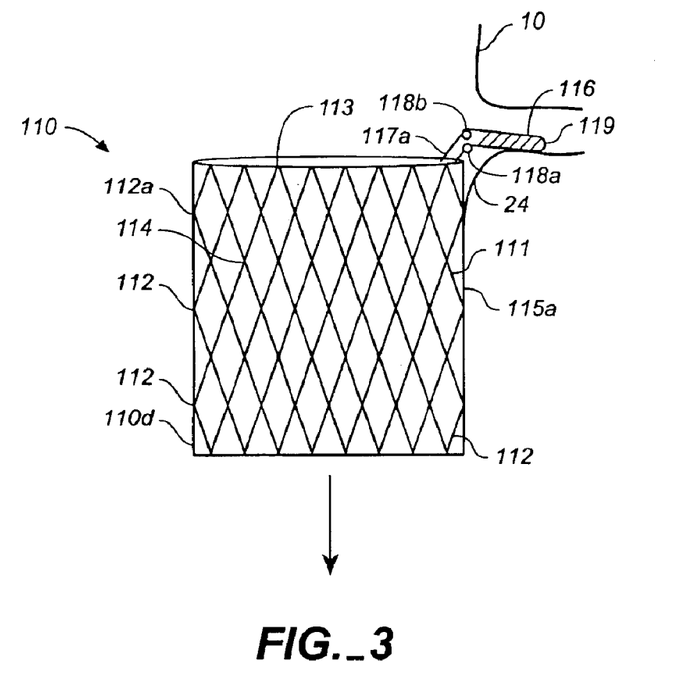
FIG. 3 is a perspective view of the cuff of FIG. 1A as the cuff is further moved distally to a fully deployed position in the aorta.

In FIG. 3, the finger member 116 is located within the renal artery 14 where the finger member 116 extends in a direction substantially laterally and radially of the sidewall 115a of the cuff 110. The finger member 116 will engage the ostium 24 of the renal artery 14 thus preventing distal migration of the cuff 110 (as the force to re-bend the finger to release it from the ostium will be generally higher than needed to prevent the cuff's release and migration—the finger acts as a stop to limit the possibility of migration).

Between the aorta-renal junction 16 and the aneurysm 18 is a region of the aorta 10 where the cuff 110 is engaged with the inner wall of the aorta 10. Annular support members 112 are designed to exert a radially outward force sufficient to bias the cuff 110 into conforming fixed engagement with the inner wall of the aorta above aneurysm 18 to support the tubular graft 115 and to provide a leak resistant seal between the cuff 110 and the inner wall of the aorta 10. The cuff 110 may be slightly longer or shorter than the area between the aorta-renal junction 16 and the aneurysm 18, which varies from patient to patient. As such the cuff 110 provides more predictable area for deploying the endoluminal prosthesis.

To deploy the cuff 110, it may be loaded into a catheter in a collapsed small diameter configuration. Annular members 112 are held in a radially compressed position by a sheath or cover placed over the cuff 110 to facilitate its delivery. The cuff 110 is delivered in a collapsed constrained configuration via the catheter through a surgically accessed femoral artery, to the desired deployment site below the aorta-renal junction 16. The sheath of the catheter positioned over the cuff 110 is retracted when the distal end of the catheter is located at the deployment site within the cuff 110 releasing the annular members 112 from the compressed position to an expanded position engaging the inner wall of the aorta 10. The cuff 110 is positioned as described herein with respect to FIGS. 1A–3.

Figure 6:
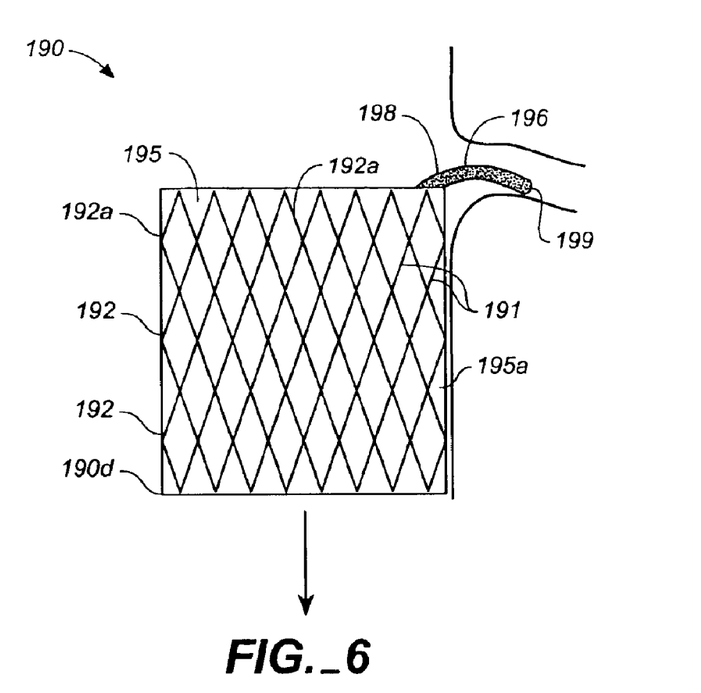
FIG. 6 is a side view with a partial cross section of an another embodiment of a prosthesis according to the invention.
Figure 7:
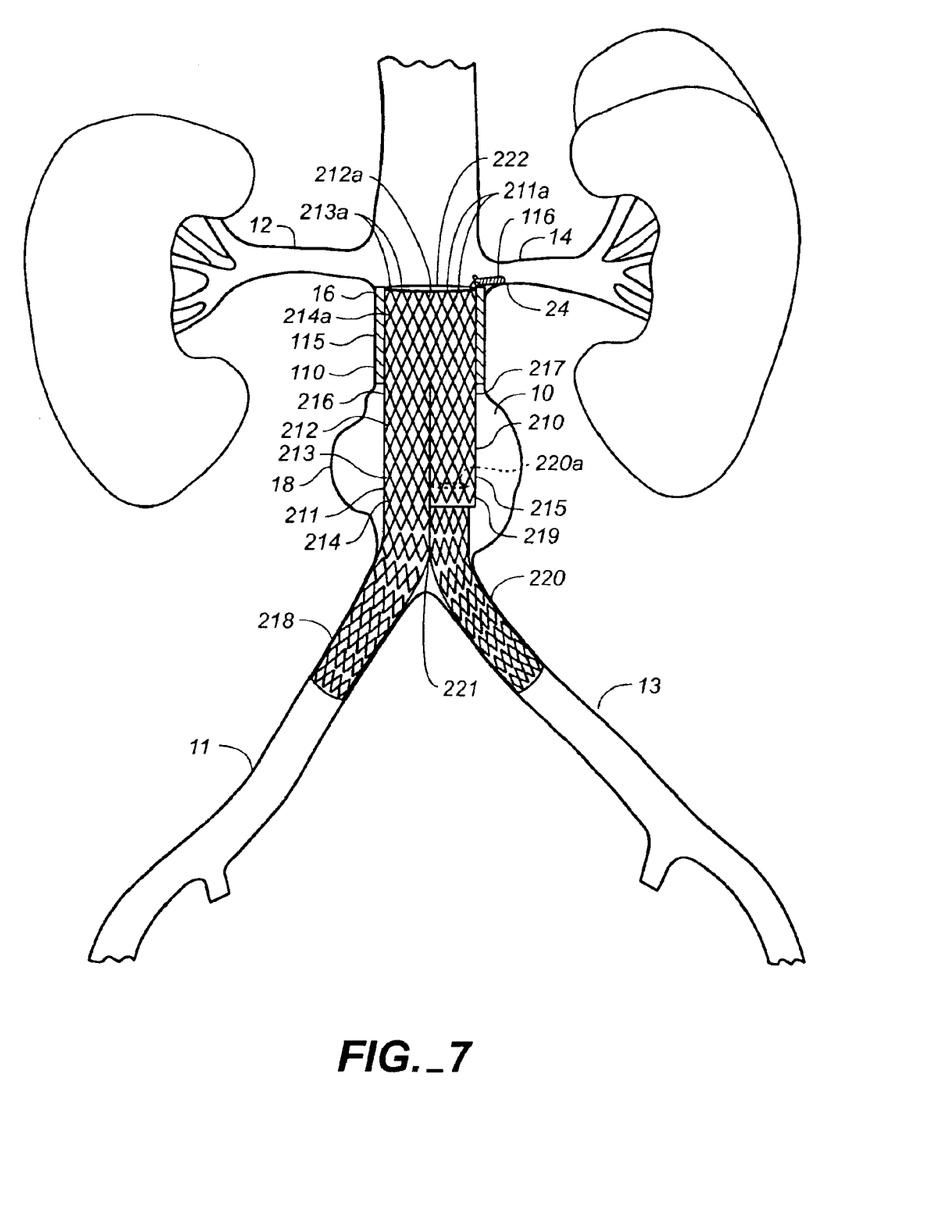
FIG. 7 is a side view and partial cross section of a long prosthesis in place in the cuff of FIGS. 1A–3 located in an aorta.

FIG. 7 illustrates an endoluminal prosthesis 210 after it has been deployed within the cuff 110 of FIGS. 1A–3. A similar prosthesis may be deployed in the cuffs 120, 140 and 190 of FIGS. 4A–4C, 5A–5C and 6 respectively.

In FIG. 7, the prosthesis 210 comprises a tubular graft 215 and a series of radially compressible annular support members 212 attached to tubular graft 215. In FIG. 7, the annular support members 212 are in an expanded position. Prior to deployment the annular members 212 are compressed. The annular members 212 support the graft and/or bias the prosthesis 210 into conforming fixed engagement with an interior surface of the cuff 110. The annular support members 212 are preferably spring members having predetermined radii and are preferably constructed of a material such as Nitinol in a superelastic, straight annealed condition.

The tubular graft 215 is preferably formed of a biocompatible, low-porosity woven fabric, such as a woven polyester. The graft material is thin-walled so that it may be compressed into a small diameter, yet capable of acting as a strong, leak-resistant, fluid conduit when in tubular form. In this embodiment, the annular support members 212 are sewn on to the outside of the tubular graft 215 material by sutures. Alternative mechanisms of attachment may be used and the annular support members 212 may be attached to the inside of the tubular graft 215. The support members 212 comprise a series of connected diamond structures 211 around the circumference of the annular member 212 that form peaks 213 and valleys 214.

The prosthesis 210 includes a main body portion 216 and a contralateral iliac extension limb 220. The main body portion 216 is a tubular bifurcated member having an aortic portion 217, a long ipsilateral iliac limb portion 218, and a short iliac portion 219. The diamond structures 211a around the circumference of the proximal most annular member 212a form peaks 213a and valleys 214a where the valleys 214a form protrusions (not shown) extending in a circumferential direction from the tubular graft 215. When deployed, the prosthesis 210 may be maneuvered so that the protrusions (not shown) engage the graft material or threads of the graft material of the tubular member 115 of the cuff 110.

As illustrated in FIG. 7, the proximal end 222 of the prosthesis 210 is placed within the cuff 110, which is placed within the aorta-renal junction 16 in the abdominal aorta 10 as described herein with reference to FIGS. 1A–3. Annular support members 212 are designed to exert a radially outward force sufficient to bias the tubular graft 215 of the endoluminal prosthesis 210 into conforming fixed engagement with the interior surface of the cuff 110 to support the tubular graft 215, and/or to provide a leak resistant seal between the prosthesis 210 and the cuff 110 which provides a seal between itself and the inner wall of the aorta 10. The proximal aortic portion 222 of the prosthesis 210 is located within cuff 110, and the long ipsilateral iliac portion limb 218 is located within the right iliac vessel 11. After deployment of the main body portion 216, the contralateral iliac extension limb 220 is located within left iliac vessel 13, and near the graft junction 221 within the short iliac portion 219. The proximal end 220a of the contralateral iliac extension limb 220 includes a proximal support member (not shown)

biasing the proximal end 220a into conforming fixed engagement with the interior surface the short iliac portion 219.

To deploy the prosthesis 210, the main body portion 216 of the prosthesis may be loaded into a catheter in a collapsed configuration where a sheath or cover placed over the prosthesis 210 holds the annular members 212 in a radially compressed position. The main body portion 216 is delivered in a compressed configuration via the catheter through a surgically accessed femoral artery, to the desired deployment site. The sheath placed over the prosthesis 210 is retracted when the distal end of the catheter is located at the deployment site within the cuff 110. The annular members 212 are then released from the compressed position to an expanded position. The proximal annular members 212 engage the inner wall of the cuff 110 while the remaining portion extends distally through the aorta 10 beyond the aneurysm 18 with the long ipsilateral limb portion 218 extending into the right iliac vessel 11. Protrusions from the annular support member 212a of the prosthesis 210 may engage the material of the inner tubular graft 115 of the cuff 110 as the prosthesis 210 is pulled distally through the cuff 110 to position the prosthesis to provide additional fixation.

Figure 4A:
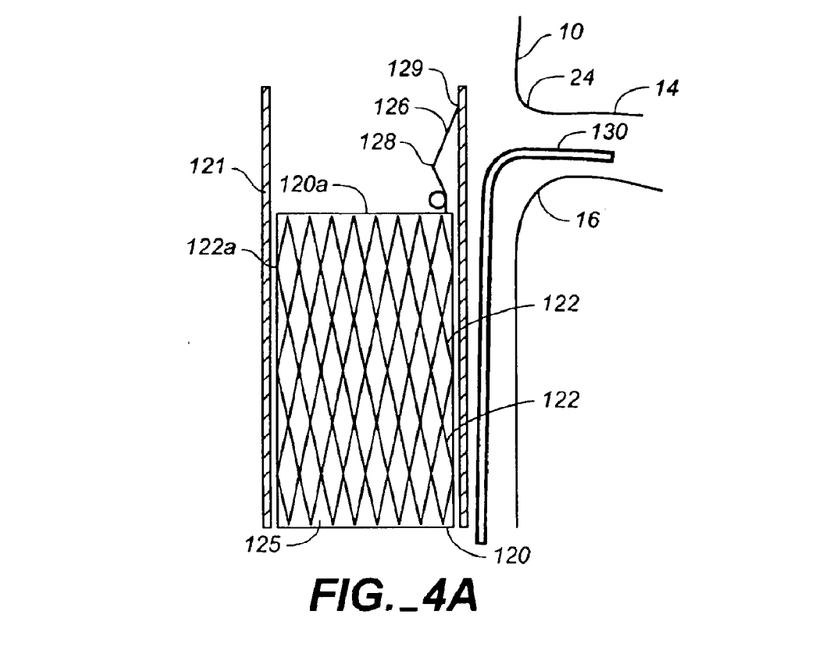
FIG. 4A is a side view of another embodiment according to the invention with the cuff covered by a sheath in place for deployment in an aorta.
Figure 4B:
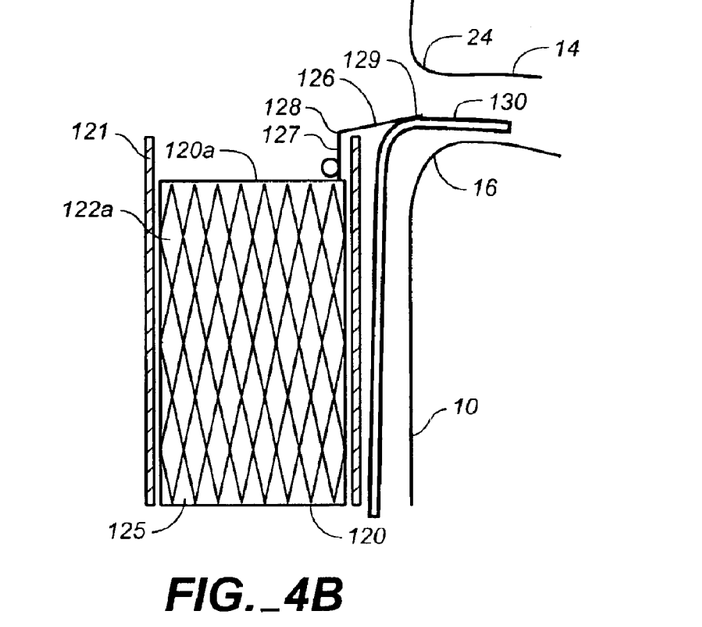
FIG. 4B is a side view of the cuff of FIG. 4A as the sheath is initially retracted.
Figure 4C:
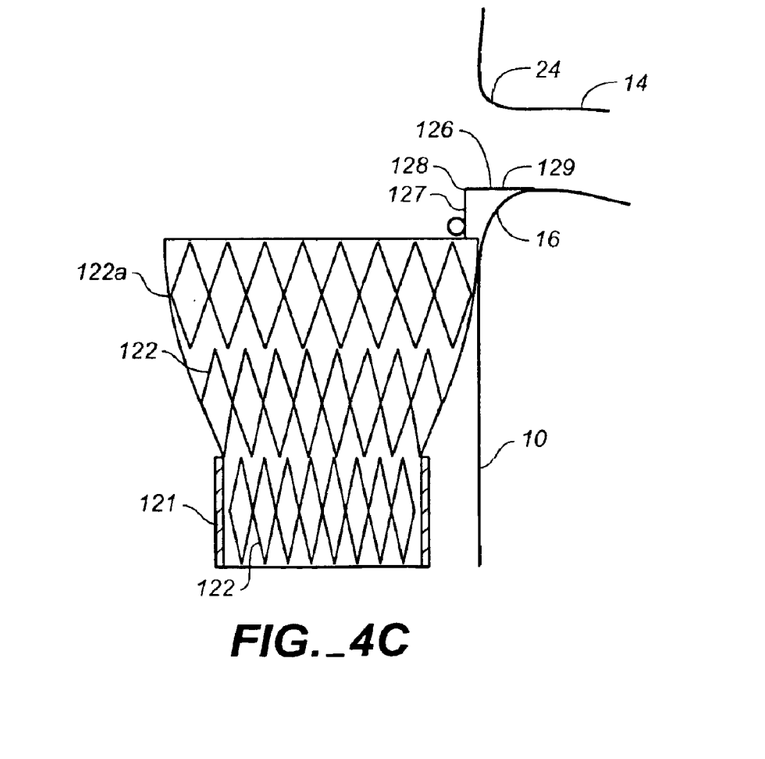
FIG. 4C is a side view of the cuff of FIG. 4A as the sheath is further retracted and the finger is located in the ostium.

FIGS. 4A–4C illustrate another embodiment of a cuff according to the invention. The cuff 120 comprises a tubular graft layer 125, a series of radially compressible annular support members 122 attached to the tubular graft layer 125, and a finger member 126 tending to extend laterally of the proximal most support member 122a. The finger member 126 is welded to the proximal most support member 122a and is configured to extend 1 or 2 millimeters above the cuff 120 when in its deployed position. The cuff 120 is constructed in a similar manner as the cuff 110 described above with reference to FIGS. 1A–3 and is used with a prosthesis in a manner similar to the use of the cuff 110 with prosthesis 210 described herein with reference to FIG. 7.

The finger member 126 is preferably a spring wire having a first portion 127 attached to the distal portion of the support member 122a, an elbow 128 where the finger member bends, and a free end 129, free from the cuff 120. The finger member 126 is illustrated in FIG. 4A in a position in which it is constrained by a sheath 121 of a catheter into which the cuff 120 is loaded. In this position the free end 129 extends in a direction proximal of the proximal end 120a of the cuff 120.

As illustrated in FIG. 4A, a guidewire 130 is inserted within the aorta, along the side of the sheath 121, and into the renal artery 14. The guidewire 130 which can be seen by fluoroscopy, provides a mechanism for locating the renal artery when deploying the finger 126 into the renal artery 14. The cuff 120 is located so that the finger is adjacent the renal artery 14. Various imaging techniques may be used to orient the catheter sheath 121 including various radiopaque markers (not shown) on the cuff 120 and/or sheath 121.

Referring to FIG. 4B, the sheath 121 is retracted and the finger member 126 tends to rotate towards a lateral position illustrated in FIG. 4B until the free end 129 is at the opening into the ostium 24 of the renal artery 14. At this time the catheter may be repositioned so that the finger 126 is more precisely located at the ostium 24. (The length of the finger in a pivoting configuration is no longer than the diameter of the branch vessel into which the finger is to be pivoted into place, and is usually somewhat shorter than the diameter of the branch vessel (otherwise pivoting of the finger may be prevented)).

Referring to FIG. 4C, the sheath 121 is then further retracted to deploy the cuff 120. The support members 122 expand to engage the inner wall of the aorta 10 at the aorta-renal junction 16 while the finger member 126 is located within the renal artery 14 where the finger member 126 extends slightly above the cuff 120 with the free end 129 extending in a direction laterally (radially of the cuff 120) of the elbow 128 of the finger member 126 to engage the ostium 24.

Figure 5A:
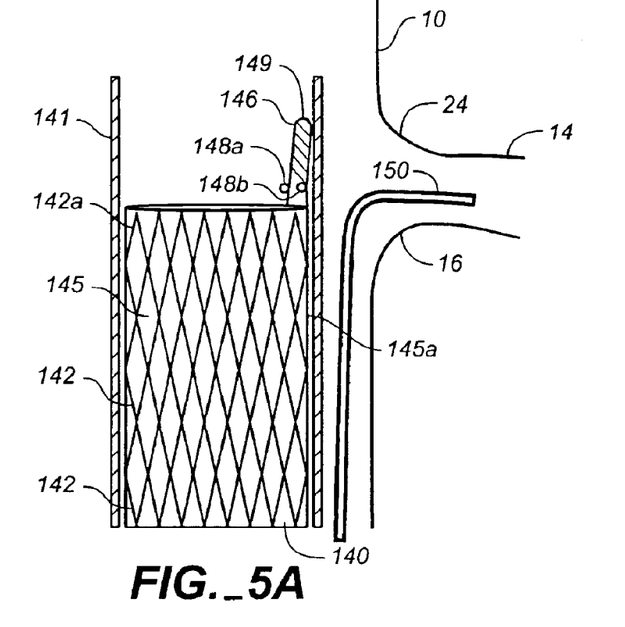
FIG. 5A is a partial cross section of another embodiment according to the invention with the cuff covered by a sheath in place for deployment in an aorta.
Figure 5B:
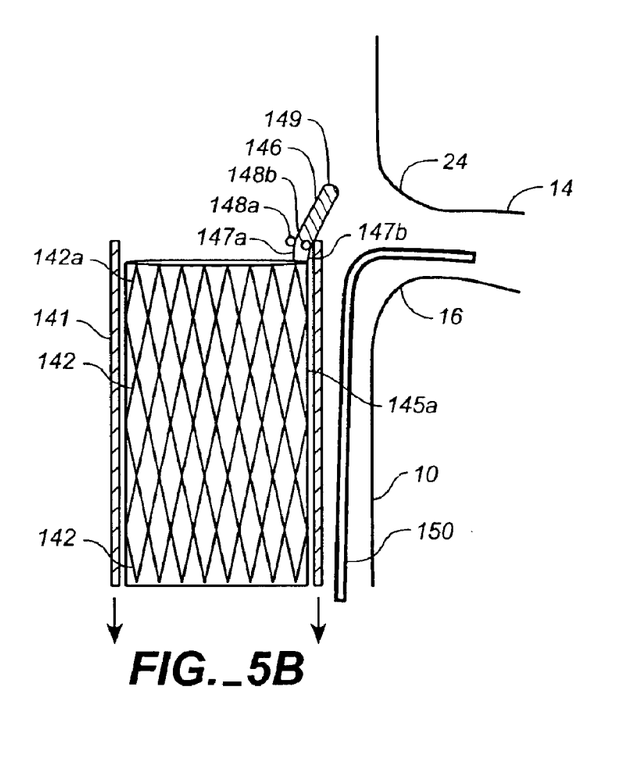
FIG. 5B is a partial cross section of the cuff of FIG. 5A as the sheath is initially retracted.
Figure 5C:
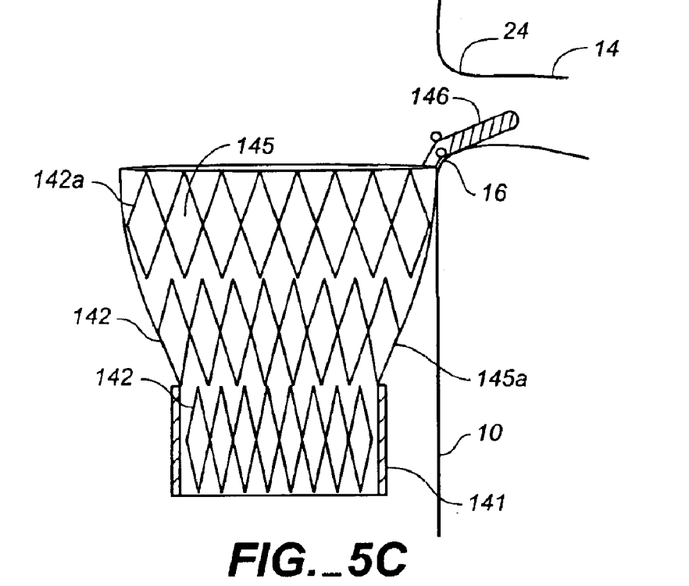
FIG. 5C is a partial cross section of the cuff of FIG. 5A as the sheath is further retracted and the finger is located in the ostium.

FIGS. 5A–5C illustrate another embodiment of a cuff according to the invention. The cuff 140 comprises a tubular graft layer 145, a series of radially compressible annular support members 142 attached to the tubular graft layer 145, and a finger member 146 tending to extend laterally of the proximal most support member 142a. The finger member 146 is welded to the proximal most support member 142a and is configured to extend 1 or 2 millimeters above the cuff 140 when in its deployed position. The cuff 140 is constructed in a similar manner as the cuff 110 described above with reference to FIGS. 1A–3 and is used with a prosthesis in a manner similar to the use of the cuff 110 with prosthesis 210 described herein with reference to FIG. 7.

The finger member 146 is preferably a spring loop made of a Nitinol wire and having a thin layer or film about the wire loop to protect adjacent tissue. The thin layer or film may be a macroporous material such as a textile or a microporous material such as a polymer film, e.g., PTFE. The textile or fiber may be wrapped around, bonded or sutured onto the loop. The finger member 146 has a first portion with members 147a, 147b attached to the distal portion of the support member 142a, and coupled by spring loops 148a, 148b to a free end 149, free from the cuff 140. The finger member 146 is shape set to a position extending laterally of the cuff 140. The spring loops 148a, 148b provide flexibility to the finger member 146 and also permit variations in length of the finger member 146. The finger member 146, when loaded in a catheter or otherwise restrained, is compressed into a position that is substantially parallel to the sidewall 145a of the tubular graft 145. The finger member 146 is illustrated in FIG. 5A in a position in which it is constrained by a sheath 141 of a catheter into which the cuff 140 is loaded. In this position, the free end 149 extends proximally of the proximal end of the cuff 140. When released, the free end 149 tends to spring towards a position extending laterally of the sidewall 145a of the tubular graft 145.

As illustrated in FIG. 5A, a guidewire 150 is inserted within the aorta 10, along the side of the sheath 141, and into the renal artery 14. The guidewire 150 provides a mechanism for locating the renal artery when deploying the finger 146 into the renal artery 14. The cuff 140 is located so that the finger 146 is adjacent the renal artery 14. Various imaging techniques may be used to orient the catheter sheath 141 including various radiopaque markers (not shown) on the cuff 140 and/or sheath 141.

Referring to FIG. 5B, the sheath 141 is retracted and the finger member 146 tends to spring towards a lateral position illustrated in FIG. 5B until the free end 149 is at the opening into the ostium 24 of the renal artery 14. At this time the catheter may be repositioned so that the finger 146 is more precisely located at the ostium 24.

Referring to FIG. 5C, the sheath 141 is then further retracted to deploy the cuff 140. The support members 142 expand to engage the inner wall of the aorta 10 at the aorta-renal junction 16 while the finger member 146 is located within the renal artery 14 where the finger member 146 extends slightly above the cuff 140 with the free end 149 extending in a direction laterally or radially of the sidewall 145a of the tubular graft 145 into the ostium 24.

FIG. 6 illustrates another embodiment of a cuff. The cuff 190 comprises a tubular graft layer 195, a series of radially compressible annular support members 192 attached to the tubular graft layer 195, and a finger member 196 extending laterally of the proximal most support member 192a. The annular support members 192 and tubular graft member 195 are constructed and attached in a similar manner as the annular support members 112 and graft 115 of cuff 110 described above with reference to FIGS. 1A–3. The cuff 190 may be secured with the prosthesis 210 in a similar manner as the cuff 110 and prostheses 210 are fixed as described below.

The finger member 196 is preferably a wire made of a shape memory alloy having a first portion 198 attached to the cuff 190 and a free end 199, free from the cuff 190. The finger member is constructed of a Nickel-Titanium alloy and is welded to one or more of diamond structures 191 that form the proximal support member 192a. The wire member is preferably coated with a biocompatible material that provides a thrombo-resistant or non-thrombogenic surface, such as silicone, polyethylene, polypropylene or other polymer. The finger member 196, when loaded in a catheter or otherwise restrained, is compressed into a position that is substantially parallel to the sidewall 195a of the tubular graft 195. In this position, the free end 199 extends towards the distal portion 190d of the cuff 190. When released, the free end 199 tends to spring towards a position extending laterally of the sidewall 195a of the tubular graft 195. The cuff 190 and finger member 196 are positioned in a similar manner as cuff 110 and finger member 116 as described with reference to FIGS. 1A–3. The cuff 190 is used with a prosthesis in a manner similar to the use of the cuff 110 with prosthesis 210 described herein with reference to FIG. 7.

Figure 8:
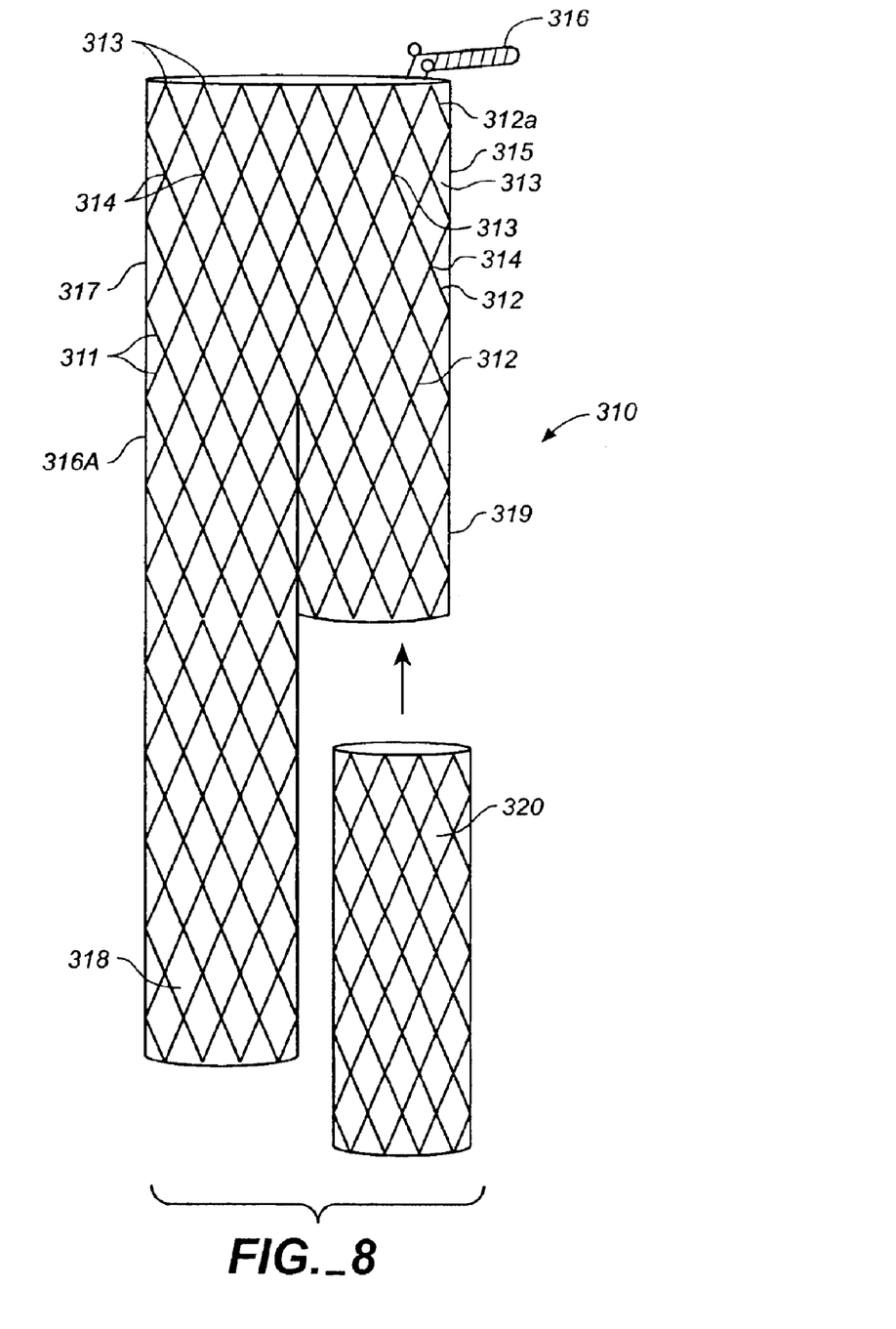
FIG. 8 is a side view with a partial cross section of another embodiment of a prosthesis according to the invention.

FIG. 8 illustrates an alternative embodiment of the invention in which a prosthesis 310 constructed in a similar manner as prosthesis 210 (FIG. 7) includes a finger member 316 for engaging an ostium of a renal artery to prevent distal migration of the prosthesis 310. The prosthesis 310 comprises a tubular graft 315 and a series of radially compressible annular support members 312 attached to tubular graft 315. In this embodiment, the annular support members 312 are sewn on to the outside of the tubular graft 315 material by sutures. The support members 312 comprise a series of connected diamond structures 311 around the circumference of the annular member 312 that form peaks 313 and valleys 314. The prosthesis 310 includes a main body portion 316A and a contralateral iliac extension limb 320. The main body portion 316A is a tubular bifurcated member having an aortic portion 317, a long ipsilateral iliac limb portion 318, and a short iliac portion 319. When the prosthesis 310 is fully deployed, the contralateral extensions 320 extends from the short iliac portion 319 of the main body 316A.

The finger member 316 is constructed in a similar manner as finger member 116 (FIGS. 1A–3 and 8) and is welded to a proximal most support structure 312a. The finger member 316 and the prosthesis 310 are deployed in a similar manner as the finger member 116 and cuff 110 described herein except that the prosthesis 310 is deployed to completely bypass the aneurysm.

In the embodiments described herein, the prosthesis may include radiopaque markers that are positioned in a manner in which rotational alignment may be determined prior to deploying the finger member. Such markers are generally know to one of skill in the art.

While the invention has been described with reference to particular embodiments, it will be understood to one skilled in the art that variations and modifications may be made in form and detail without departing from the spirit and scope of the invention.

What is claimed is:

1. An endoluminal prosthesis comprising:
   a tubular graft comprising a graft material forming an opening and a lumen for the flow of body fluid therethrough;
   at least one annular support member coupled to the graft material for supporting the graft material to provide the lumen for the flow of body fluid through the tubular graft;
   a proximal end portion; and
   a protruding member coupled to the proximal end portion of the prosthesis and extending radially outward with respect to an axis extending through the opening and proximally of the tubular graft, the protruding member comprising a first portion coupled to the prosthesis and a free end portion wherein the first portion of the protruding member is coupled to an elbow portion and forming a bend in the protruding member, and which is coupled to the free end portion so that the elbow portion is located between the first portion and the free end portion, wherein the protruding member comprises a spring biased so that the free end portion tends to extend outward with respect to the axis extending through the opening of the tubular graft.

2. An endoluminal prosthesis comprising:
   a tubular graft comprising a graft material forming an opening and a lumen for the flow of body fluid therethrough;
   at least one annular support member coupled to the graft material for supporting the graft material to provide the lumen for the flow of body fluid through the tubular graft; and
   a protruding member coupled to the prosthesis and protruding radially outward with respect to an axis extending through the opening of the tubular graft wherein the protruding member comprises a first portion coupled to the annular support member and a free end portion and a spring member located between the first portion and the free end portion, wherein the spring member is biased so that the free end portion tends to extend radially outward with respect to the axis extending through the opening, from the annular support member.

3. The endoluminal prosthesis of claim 2 wherein the tubular graft of the endoluminal prosthesis has the axis extending through the opening, and wherein the protruding member has a compressed configuration wherein the protruding member extends axially away from the tubular graft.

4. An endoluminal prosthesis comprising:
   a tubular graft comprising a graft material forming an opening and a lumen for the flow of body fluid therethrough;
   at least one annular support member coupled to the graft material for supporting the graft material to provide the lumen for the flow of body fluid through the tubular graft; and
   a protruding member coupled to the prosthesis and protruding radially outward with respect to an axis extending through the opening of the tubular graft wherein the protruding member comprises a spring member having a first portion coupled to the annular support member and a free end portion wherein the spring member is biased so that the free end portion tends to extend radially outward with respect to the axis extending through the opening, from the annular support member;

wherein the tubular graft of the endoluminal prosthesis has the axis extending through the opening, and wherein the protruding member has a compressed configuration wherein the protruding member extends axially along the tubular graft.

5. An endoluminal prosthesis comprising:
a tubular graft comprising a graft material forming an opening and a lumen for the flow of body fluid therethrough;
at least one annular support member coupled to the graft material for supporting the graft material to provide the lumen for the flow of body fluid therethrough; and
a protruding member coupled to the prosthesis and protruding radially outward with respect to an axis extending through the opening, of the tubular graft, wherein the protruding member is coupled to the at least one annular support member and wherein a portion of the protruding member is configured to be deployed upstream of a branch vessel and moved downstream until it is positioned within the branch vessel through an ostium of the branch vessel as the prosthesis is being deployed so as to engage the branch vessel and reduce distal migration of the prosthesis.

6. The endoluminal prosthesis of claim 5 wherein the protruding member comprises a wire.

7. The endoluminal prosthesis of claim 6 wherein the wire is coated with a thrombo-resistant material.

8. The endoluminal prosthesis of claim 5 wherein the protruding member comprises a loop.

9. An endoluminal prosthesis comprising:
a cuff comprising a tubular member comprising at least one annular support member and having an opening configured to receive a tubular prosthesis therein to provide a lumen for the flow of body fluid through the cuff and the prosthesis; and
a protruding member coupled to the cuff and protruding radially outward with respect to an axis extending through the opening, of the tubular member and wherein the protruding member is configured to be deployed upstream of a branch vessel and moved downstream until it is positioned within the branch vessel through an ostium of the branch vessel as the cuff is being deployed so as to engage the branch vessel and reduce distal migration of the prosthesis.

10. The endoluminal prosthesis of claim 9 wherein the protruding member is coupled to the at least one annular support member.

11. The endoluminal prosthesis of claim 9 wherein the protruding member comprises a wire.

12. The endoluminal prosthesis of claim 9 wherein the protruding member comprises a loop.

13. An endoluminal prosthesis comprising:
a cuff comprising a tubular member comprising at least one annular support member and having an opening configured to receive a tubular prosthesis therein to provide a lumen for the flow of body fluid through the cuff and the prosthesis; and
a protruding member coupled to the cuff and protruding radially outward with respect to an axis extending through the opening, of the tubular member and wherein the protruding member is configured to be deployed upstream of a branch vessel and moved downstream until it is positioned within the branch vessel as the cuff is being deployed so as to engage the branch vessel and reduce distal migration of the prosthesis, wherein the protruding member comprises a spring member having a first portion coupled to the cuff and a free end portion wherein the spring member is biased so that the free end portion tends to extend outward with respect to the axis extending through the opening of the cuff.

14. A modular endoluminal prosthesis comprising:
a) a cuff comprising a tubular member having an opening configured to receive a tubular prosthesis and a protruding member coupled to the cuff and protruding radially outward with respect to an axis extending through the opening of the tubular member wherein the protruding member is configured to be deployed upstream of a branch vessel and moved downstream until it is positioned within the branch vessel through an ostium of the branch vessel as the cuff is deployed so as to engage the branch vessel and reduce distal migration of the prosthesis; and
b) an elongate tubular prosthesis comprising:
a tubular graft comprising a graft material forming a lumen for the flow of body fluid therethrough; and
at least one annular support member coupled to the graft material for supporting the graft material to provide the lumen for the flow of body fluid therethrough,
wherein a portion of the elongate tubular prosthesis is configured to fit within the opening in the cuff and to engage the cuff to form a leak resistant seal therewith.

15. The modular endoluminal prosthesis of claim 14 wherein the protruding member comprises a spring member having a first portion coupled to the cuff and a free end portion wherein the spring member is biased so that the free end portion tends to extend outward with respect to the axis extending through the opening of the cuff.

16. The modular endoluminal prosthesis of claim 14 wherein the protruding member comprises a wire.

17. The modular endoluminal prosthesis of claim 14 wherein the protruding member comprises a loop.

18. A method for excluding a diseased portion of a body lumen from the flow of body fluid comprising the steps of:
providing a cuff comprising a tubular member having an opening configured to receive a tubular prosthesis therein; and a protruding member coupled to the cuff and protruding radially outward with respect to an axis extending through the opening, of the tubular member;
locating the cuff in a constrained configuration with the protruding member within the body lumen upstream of the diseased portion of the body lumen;
releasing at least a portion of the cuff and the protruding member from the constrained configuration so that the protruding member is adjacent a tributary vessel; and
then repositioning the protruding member so that it extends within the tributary vessel through an ostium of the tributary vessel and fixing the cuff to an inner wall of the body lumen at a fixation site within the body lumen at a location upstream of the diseased portion.

19. The method of claim 18 wherein the step of providing comprises providing the protruding member attached to the cuff.

20. The method for excluding a diseased portion of a body lumen from the flow of body fluid of claim 18 further comprising the steps of:
providing an endoluminal prosthesis comprising a tubular member having a proximal opening and a distal opening, the tubular member, proximal opening and distal opening forming a lumen for the flow of body fluid therethrough;

locating a portion of the endoluminal prosthesis within the opening in the cuff;

fixing the portion of the endoluminal prosthesis to the cuff; and deploying the endoluminal prosthesis in the body lumen to bypass the diseased portion of the body lumen and to provide the lumen for the flow of body fluid therethrough.

21. The method of claim 20 wherein the opening in the cuff is a distal opening, and wherein the step of locating the portion of the endoluminal prosthesis within the opening in the cuff comprises locating a portion of the prosthesis including the proximal opening in the prosthesis, through the distal opening in the cuff and deploying the portion of the prosthesis within the cuff adjacent the distal opening of the cuff.

22. A method for excluding a diseased portion of a body lumen from the flow of body fluid comprising the steps of:

providing an endoluminal prosthesis comprising:
a tubular graft comprising a graft material forming an opening and a lumen for the flow of body fluid therethrough;
at least one annular support member coupled to the graft material for supporting the graft material to provide the lumen for the flow of body fluid therethrough;
a spring member coupled to the prosthesis wherein the spring member tends to protrude radially outward from the prosthesis with respect to an axis extending through the opening;

delivering the prosthesis in a constrained configuration to an aneurysm site for deployment of the prosthesis, wherein the deployment site includes a first vessel having an aneurysm and at least one tributary vessel of the first vessel, upstream of the aneurysm;

positioning the prosthesis within the first vessel with the spring member adjacent the at least one tributary vessel; and releasing and repositioning the prosthesis from the constrained configuration so that the spring member is located within the at least one tributary vessel through an ostium of the tributary vessel in a configuration protruding radially outward from the prosthesis with respect to the axis extending through the opening.

23. An endoluminal prosthesis comprising:
a cuff means for fixing a prosthesis means above an aneurysm within a body lumen, including a protruding means for being released adjacent a junction of a side vessel and a body lumen upstream of the aneurysm within the body lumen and for being repositioned to engage the junction of the side vessel and body lumen through an ostium of the side vessel as the cuff means is released and deployed within the body lumen.

24. The endoluminal prosthesis of claim 23 wherein the cuff means comprises a tubular means having an opening and including a coupling means for coupling the tubular means to an inner wall of the body lumen and for forming a leak resistant seal with the inner wall of the body lumen.

25. The endoluminal prosthesis of claim 24 further comprising:
an elongate prosthesis means comprising:
a tubular graft means for providing a lumen for the flow of body fluid therethrough;
at least one annular support means coupled to the graft means, the support means for supporting the graft means to provide the lumen for the flow of body fluid therethrough,
wherein a portion of the elongate prosthesis means is configured to fit within the opening in the cuff means.

26. An endoluminal prosthesis comprising:
a tubular graft means for providing a lumen for the flow of body fluid therethrough;
at least one annular support means coupled to the graft means, the support means for supporting the graft means to provide the lumen for the flow of body fluid therethrough; and
a protruding means for being released adjacent a junction of a side vessel and a body lumen upstream of a diseased portion of the body lumen and for being repositioned to engage the junction of the side vessel and body lumen through an ostium of the side vessel as the annular support means is released and deployed within the body lumen.

* * * * *